United States Patent [19]

Kalmar

[11] 4,308,862
[45] Jan. 5, 1982

[54] PLASTER CAST

[76] Inventor: Irene Kalmar, 49 Young St., Sylvania, New South Wales 2224, Australia

[21] Appl. No.: 119,234

[22] Filed: Feb. 6, 1980

[30] Foreign Application Priority Data

Feb. 14, 1979 [AU] Australia .............................. PD7675

[51] Int. Cl.³ ............................................. A61F 13/04
[52] U.S. Cl. .................................................. 128/91 R
[58] Field of Search ...................... 128/87 R, 89 R, 90, 128/91 R, 91 A, 165, 24 R, 60, 64

[56] References Cited

U.S. PATENT DOCUMENTS

| 2,206,339 | 7/1940 | Ulman, Jr. | 128/91 A |
| 2,731,963 | 1/1956 | Blank | 128/91 A |
| 2,837,088 | 6/1958 | Moses | 128/91 A |
| 3,116,731 | 1/1964 | Baxter | 128/91 R |
| 3,477,427 | 11/1969 | Lapidus | 128/82.1 |
| 3,505,990 | 4/1970 | Hawkins | 128/24 R |
| 3,701,349 | 10/1972 | Larson | 128/89 R |
| 3,826,252 | 7/1974 | Laico | 128/91 R |
| 3,998,220 | 12/1976 | Cleer, Jr. et al. | 128/91 R |
| 4,019,506 | 4/1977 | Eschmann | 128/90 |

FOREIGN PATENT DOCUMENTS 587069 10/1933 Fed. Rep. of Germany ... 128/91 A

*Primary Examiner*—Robert W. Michell
*Assistant Examiner*—Arthur S. Rose
*Attorney, Agent, or Firm*—Ladas & Parry

[57] ABSTRACT

A support or cast for immobilising broken limbs is disclosed. The cast is formed from an inner air permeable layer, for example lint, and an outer rigid casing. Tubes with spaced apertures opening onto the inner layer are located between the inner and outer layers. Preferably air is pumped into the tubes to pass into the inner layer and thence out of the support. Such ventilation prevents discomfort and itching.

4 Claims, 4 Drawing Figures

PLASTER CAST

The present invention relates to supports or casts of the type used in the medical field to rigidly support a limb of a wearer of the cast and also relates to methods of applying such supports and to articles used in such supports.

It is a disadvantage of presently known casts, and in particular plaster casts, that the skin covered by the case becomes irritated and itchy. This results in great discomfort for the patient, particularly when the cast must be worn for a substantial length of time.

Hitherto this problem has been to some extent ameliorated by the relatively frequent removal and replacement of such casts. U.S. Pat. No. 4,019,506 discloses a cast with means for facilitating the easy removal of the cast. In addition, the abovementioned U.S. patent also discloses a complicated constructional arrangement which, to some extent, permits the limb encased in the cast to "breathe", thereby reducing itchiness.

It is an object of the present invention to provide a simplified cast or support construction which permits adequate ventilation of the limb encased by the cast, thereby substantially reducing the degree of irritation experienced by the user.

According to one aspect of the present invention there is disclosed a support to surround an immobilise a limb of a wearer of the support, said support comprising a layer of flexible air permeable material immediately adjacent to, and surrounding said limb; conduit means positioned adjacent said air permeable material and having a plurality of spaced apertures therethrough communicating with said air permeable material; a substantially rigid casing enveloping said air permeable material and said conduit means to retain same in position; and vent means permitting communication between said conduit means and the exterior of said casing.

Methods of applying a support in accordance with the present invention are also disclosed as are articles useful in the construction of such a support.

Embodiments of the present invention will now be described with reference to the drawings in which.

Figure 1:
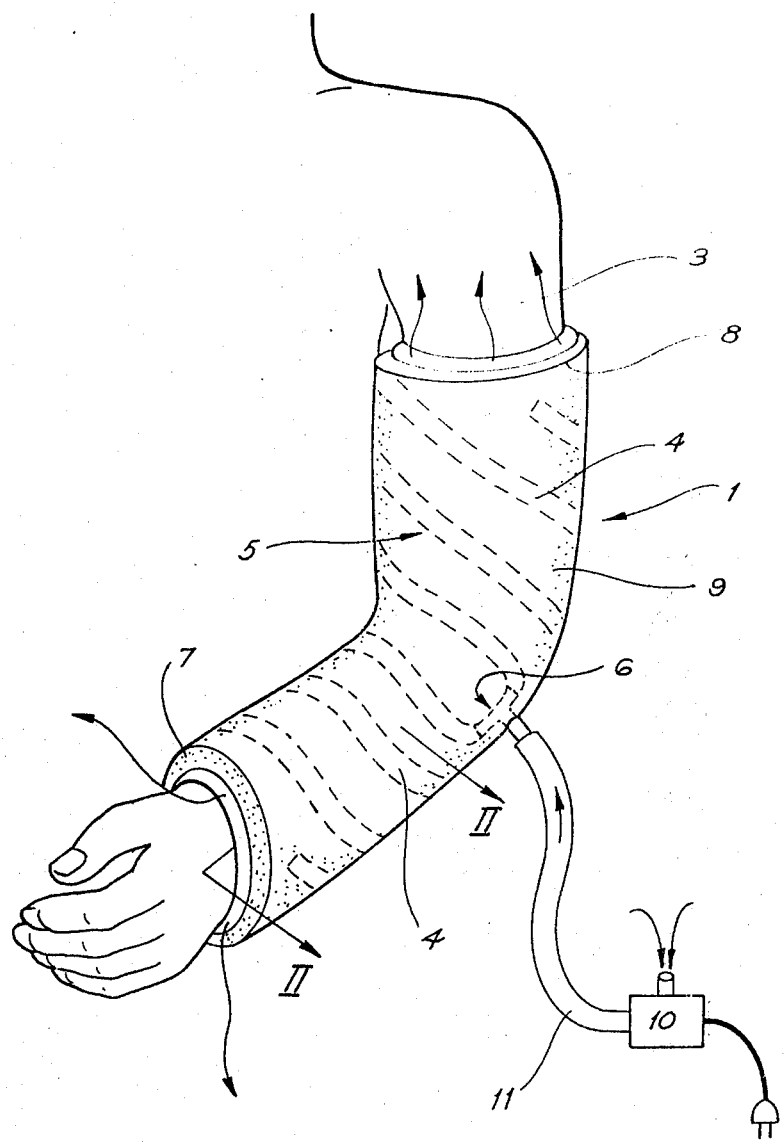
FIG. 1 is a perspective view of the support of the preferred embodiment.
Figure 2:
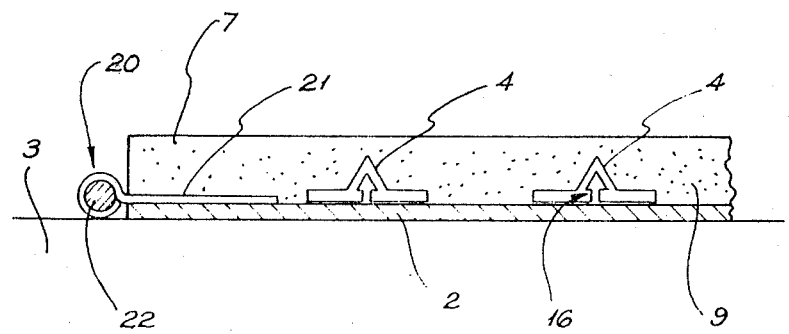
FIG. 2 is a cross-sectional view taken along the line II—II of FIG. 1.

Turning now to FIGS. 1 and 2, the cast or support 1 of the preferred embodiment comprises an inner layer 2 of air permeable material such as lint or other similar known dressing material which is applied directly to the limb 3 of the wearer.

Surrounding the inner layer 2, are two lengths of flexible plastics tubing 4, each of which is preferably wound around the inner layer 2 in the form of a spiral or helix 5 as indicated by dash lines in FIG. 1. One end of each of the lengths of tubing 4 is pushed over the corresponding end of the cross portion of a T-shaped pipe 6 which is located approximately equi-distant from the ends 7 and 8 of the support 1. The other ends of the lengths of tubing 4 are located adjacent the corresponding ends 7 and 8.

The stem of the T-shaped pipe 6 protrudes beyond the support 1 and is releasably connectable to an electrically operated air pump 10 by means of an air hose 11.

Figure 3:
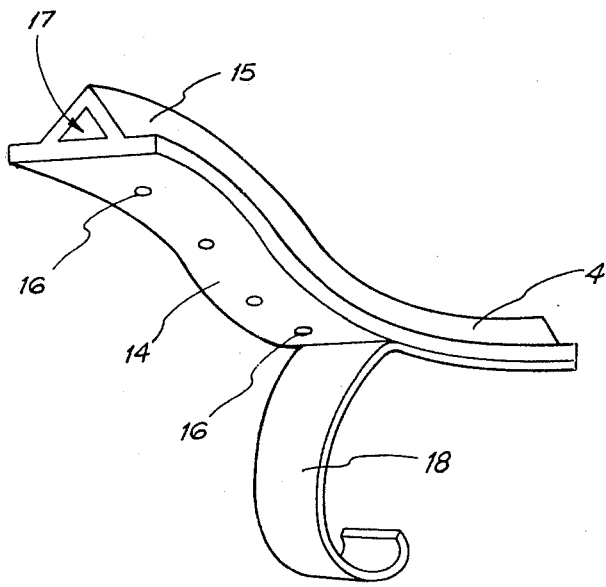
FIG. 3 is a perspective view of a portion of one embodiment of the conduits used in FIGS. 1 and 2.

As best seen in FIG. 3, the tubing 4 comprises a flat surface 14 surmounted by a hollow ridge 15, which results in the tubing 4 having a generally triangular cross section. A plurality of spaced apertures 16 are located in the flat surface 14 and permit communication between the flat surface 14 and the interior 17 of the tubing 4.

As best seen in FIG. 2, the tubing 4 is placed over the inner layer 2 so that the flat surface 14 abuts the inner layer 2. With the tubing 4 so located, a flowable hardenable material such as plaster or resin is applied to the inner layer 2 and tubing 4 in order to provide a rigid casing 9 which envelopes the inner layer 2 and tubing 4.

It is of assistance in locating the tubing 4 on the inner layer 2 if the flat surface 14 has an adhesive applied thereto. Such an adhesive is not essential. However, when such an adhesive is used the flat surface 14 of the tubing 4 is preferably covered by a peel off layer 18 (FIG. 3).

In order to increase the comfort of the wearer of the support 1, a padding buffer 20 is preferably provided. The buffer 20 takes the form of a strip of, preferably air permeable, adhesive material which is applied to the end of the inner layer 2 so that a portion of the adhesive material 21 protrudes beyond what will become the end 7 of the support 1. That portion of the strip of adhesive material 21 which protrudes beyond the casing 9 surrounds an annular wad 22, thereby retaining the wad 22 in place between the limb 3 and end 7.

In order to reduce the discomfort of the wearer of the support 1 air, preferably including a small amount of disinfectant or other medical substance, is pumped via the pump 10 through the air hose 11 and into the T-shaped pipe 6. The air is then able to move along the tubing 4 and out through the apertures 16 therein so as to pass into the air permeable layer 2. Ultimately, the air passes next to the skin of the limb 3 and finally beyond the ends 7 and 8 of the support 1 as indicated by arrows in FIG. 1.

In this way, the surface of the skin of the limb 3 is ventilated, thereby evaporating and carrying away any perspiration, cooling the limb 3, allowing the skin of the limb 3 to "breathe", and so on.

Naturally, it is not necessary that the support 1 be ventilated by the pump 10 continuously, and therefore the air hose 11 is preferably releasably secured to the stem of the T-shaped pipe 6. Thus the wearer of the support 1 is able to move about and only ventilate the support 1 during periods of inactivity, such as when watching television.

Figure 4:
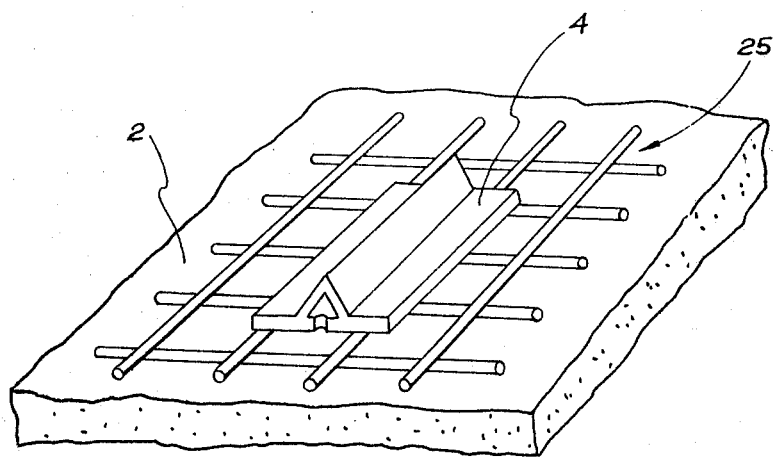
FIG. 4 is a perspective view of a portion of an alternative embodiment to that of FIG. 3.

FIG. 4 illustrates an alternative embodiment for the construction of the inner layer 2 and tubing 4. In the construction illustrated schematically in FIG. 4, a mesh 25 formed from welded filaments of plastics material, such as that commonly used to provide see-through plastic bags for fruit such as oranges, is provided. The tubing 4 is bonded by means such as plastics welding to the mesh 25. In one form a strip of mesh 25 to which the tubing 4 has been bonded is supplied and then wrapped around the inner layer 2 in a manner substantially similar to that illustrated in FIGS. 1 and 2.

Alternatively, a strip of air permeable material can be bonded, or otherwise secured, to the mesh 25 and the resulting material wound in a helix around the limb 3 in order to locate the inner layer 2 and tubing 4 in a single operation.

The foregoing describes only some embodiments of the present invention and modifications, obvious to those skilled in the art, may be made thereto without departing from the scope of the present invention. For example, the tubing 4 can be arranged in a single length and/or arranged to extend longitudinally rather than transversely in a helical or spiral form as illustrated. In addition, for relatively long casts, from thigh to ankle for example, a plurality of T-shaped pieces 6 are preferably used. These pieces 6 are regularly spaced along the cast and each supplied with air from pump 10 to give a uniform result along the length of the cast.

What I claim is:

1. A support shaped such that when positioned on a limb of the wearer of said support, said support will surround and immobilise said limb, said support comprising a layer of flexible air permeable material adapted to lie immediately adjacent to, and surround, said limb; a substantially rigid casing have two ends and enveloping said layer; a substantially T-shaped pipe positioned between said layer and said casing with the stem of said pipe protruding through said casing approximately equi-distant from said ends; two lengths of flexible plastics tubing located between said layer and said casing and each having one end thereof joined to a corresponding end of the cross position of said pipe, both said lengths of tubing being helically wound over said layer so as to extend in opposite directions away from said T-shaped pipe, said tubing having a substantially flat surface abutting said layer and a plurality of spaced apertures extending through said flat surface; and an air pump adapted to be coupled to said stem whereby said layer, pipe and tubing are maintained in position by said casing and said pump permits air to be forced into said air permeable material via said tubing, said air evaporating perspiration and leaving said support at said ends of said casing.

2. A support as claimed in claim 1 wherein an end of said support is terminated by a strip of adhesive material, said strip being interposed between said casing and said air permeable material, being adhered to said air permeable material and protruding beyond the corresponding end of said casing, that portion of said strip protruding beyond said casing enveloping a resilient wad thereby forming a padding buffer between said limb and said end of said casing.

3. A support as claimed in claim 1 wherein said flat surface has an adhesive applied thereto which, prior to location of said conduit means, is covered by a protective peel off layer.

4. A support as claimed in claim 3 wherein said flat surface is bonded to a mesh layer.

* * * * *